(12) United States Patent
Tuccelli et al.

(10) Patent No.: US 11,732,003 B2
(45) Date of Patent: Aug. 22, 2023

(54) MECHANICAL METHOD OF MAINTAINING NARROW RESIDENCE TIME DISTRIBUTIONS IN CONTINUOUS FLOW SYSTEMS

(71) Applicant: EMD Millipore Corporation, Burlington, MA (US)

(72) Inventors: Ronald Tuccelli, Burlington, MA (US); John Caulmare, Burlington, MA (US); Luc Messier, Burlington, MA (US); Melissa Holstein, Burlington, MA (US); Christopher Gillespie, Burlington, MA (US); Roger Hill, Burlington, MA (US)

(73) Assignee: EMD Millipore Corporation, Burlington, MA (US)

( * ) Notice: Subject to any disclaimer, the term of this patent is extended or adjusted under 35 U.S.C. 154(b) by 436 days.

(21) Appl. No.: 16/610,616

(22) PCT Filed: Apr. 18, 2018

(86) PCT No.: PCT/US2018/028101
§ 371 (c)(1),
(2) Date: Nov. 4, 2019

(87) PCT Pub. No.: WO2018/208447
PCT Pub. Date: Nov. 15, 2018

(65) Prior Publication Data
US 2020/0172568 A1 Jun. 4, 2020

Related U.S. Application Data

(60) Provisional application No. 62/504,633, filed on May 11, 2017.

(51) Int. Cl.
*A61L 2/00* (2006.01)
*A61L 2/26* (2006.01)
(Continued)

(52) U.S. Cl.
CPC .............. *C07K 1/22* (2013.01); *A61L 2/0088* (2013.01); *A61L 2/26* (2013.01); *B01D 15/245* (2013.01);
(Continued)

(58) Field of Classification Search
None
See application file for complete search history.

(56) References Cited

U.S. PATENT DOCUMENTS 3,047,367 A 7/1962 Kessler
3,479,141 A 11/1969 Smythe et al.
(Continued)

FOREIGN PATENT DOCUMENTS

AU 2013248242 A1 11/2013
CA 2983884 A1 11/2016
(Continued)

OTHER PUBLICATIONS

"About Peristaltic Pumps" published by Cole-Parmer, <https://www.coleparmer.com/tech-article/about-peristaltic-pumps>, accessed Apr. 5, 2022 (Year: 2018).*
(Continued)

*Primary Examiner* — Holly Kipouros
(74) *Attorney, Agent, or Firm* — Nields, Lemack & Frame, LLC

(57) ABSTRACT

Methods of maintaining narrow residence time distributions in continuous flow systems, particularly applicable to virus inactivation such as during a protein purification process. Fluid sample is introduced into an axial flow channel and caused to flow therein in discrete packets or zones to minimize residence time distribution and axial dispersion. Embodiments described herein obviate or minimize the need for using large tanks or reservoirs for performing virus inactivation during a protein purification process; reduce the (Continued)

overall time required for virus inactivation, and/or reduce the overall physical space required to perform the virus inactivation operation during a protein purification process, which in turn reduces the overall footprint for the purification process.

3 Claims, 9 Drawing Sheets

(51) Int. Cl.
  B01D 15/24     (2006.01)
  B01L 3/00      (2006.01)
  C12N 7/00      (2006.01)
  C07K 1/22      (2006.01)
  B01D 15/36     (2006.01)
  B01D 15/38     (2006.01)

(52) U.S. Cl.
  CPC ....... *B01D 15/361* (2013.01); *B01D 15/3809* (2013.01); *B01L 3/502* (2013.01); *C12N 7/00* (2013.01); *A61L 2202/21* (2013.01); *B01L 2400/0481* (2013.01); *B01L 2400/082* (2013.01); *C12N 2740/10063* (2013.01); *C12N 2740/10064* (2013.01); *C12N 2795/00063* (2013.01); *C12N 2795/00064* (2013.01)

(56) References Cited

U.S. PATENT DOCUMENTS

| | | | |
|---|---|---|---|
| 3,920,030 A * | 11/1975 | Mason | A61L 2/18 604/4.01 |
| 5,203,002 A | 4/1993 | Wetzel | |
| 5,304,113 A * | 4/1994 | Sieber | A61K 31/505 604/20 |
| 6,586,172 B1 | 7/2003 | Gunn et al. | |
| 6,596,230 B1 * | 7/2003 | Woo | A61M 1/3681 250/433 |
| 2002/0146338 A1 * | 10/2002 | Mittelstein | F04B 43/1261 417/474 |
| 2007/0148777 A1 | 6/2007 | Gilbert et al. | |
| 2009/0266421 A1 | 10/2009 | Linder et al. | |
| 2010/0078077 A1 | 4/2010 | Ismagilov et al. | |
| 2010/0078086 A1 | 4/2010 | Guidat et al. | |
| 2010/0171055 A1 | 7/2010 | Dourdeville | |
| 2011/0060152 A1 | 3/2011 | Dennis et al. | |
| 2014/0154670 A1 * | 6/2014 | Williams, Jr. | G01N 31/226 435/31 |
| 2015/0064769 A1 | 3/2015 | Xenopoulos | |
| 2016/0296896 A1 | 10/2016 | Reel et al. | |
| 2016/0375159 A1 | 12/2016 | Lobedann et al. | |
| 2017/0037381 A1 | 2/2017 | Coffman et al. | |
| 2017/0157566 A1 * | 6/2017 | Gefroh | B01D 61/22 |
| 2018/0228927 A1 * | 8/2018 | Ito | A61L 2/28 |
| 2019/0117803 A1 | 4/2019 | Schwan et al. | |
| 2020/0061495 A1 | 2/2020 | Tuccelli et al. | |

FOREIGN PATENT DOCUMENTS

| | | | |
|---|---|---|---|
| CN | 101652319 A | 2/2010 | |
| CN | 104411820 A | 3/2015 | |
| EP | 3088006 A1 | 11/2016 | |
| JP | 2005-514187 A | 5/2005 | |
| JP | 2008-538077 A | 10/2008 | |
| JP | 2010-506136 A | 2/2010 | |
| JP | 2008-510538 A5 | 1/2012 | |
| JP | 2015-522017 A | 8/2015 | |
| TW | 201702377 A | 1/2017 | |
| WO | 99/40384 A1 | 8/1999 | |
| WO | 03/000418 A2 | 1/2003 | |
| WO | 2006/101851 A2 | 9/2006 | |
| WO | 2008/063227 A2 | 5/2008 | |
| WO | 2009/151322 A1 | 12/2009 | |
| WO | 2011/094279 A1 | 8/2011 | |
| WO | 2014/004103 A1 | 1/2014 | |
| WO | 2015/135844 A1 | 9/2015 | |
| WO | 2015/158776 A1 | 10/2015 | |
| WO | 2016/173982 A1 | 11/2016 | |

OTHER PUBLICATIONS

International Search Report and Written Opinion dated Jul. 26, 2018 in corresponding PCT application No. PCT/US2018/028101.
International Search Report and Written Opinion dated Jul. 5, 2018 in co-pending PCT application No. PCT/US2018/028102.
Taiwanese communication, with English translation, dated Jan. 23, 2019 in corresponding Taiwanese patent application No. 107115295.
Taiwanese communication, with English translation, dated Feb. 22, 2019 in co-pending Taiwanese patent application No. 107115294.
Garstecki et al., "Formation of Bubbles and Droplets in Microfluidic Systems", Bulletin of the Polish Academy of Sciences, Technical Sciences, vol. 53, No. 4, pp. 361-372, 2005.
Tsaoulidis et al., "Effect of Channel Size on Liquid-Liquid Plug Flow in Small Channels", AIChE Journal, vol. 62, No. 1, pp. 315-324, Jan. 2016.
European communication dated Jan. 11, 2021 in corresponding European patent application No. 18799039.5.
European communication dated Dec. 21, 2020 in co-pending European patent application No. 18798437.2.
Japanese communication, with English translation, dated Mar. 2, 2021 in corresponding Japanese patent application No. 2019-561994.
Chinese communication, with English translation, dated Apr. 2, 2021 in co-pending Chinese patent application No. 201880046306.7.
Chinese communication, with English translation, dated Apr. 8, 2021 in corresponding Chinese patent application No. 201880046288.2.
Japanese communication, with English translation, dated Aug. 3, 2021 in co-pending Japanese patent application No. 2019-561961.
Japanese communication, with English translation, dated Dec. 7, 2021 in corresponding Japanese patent application No. 2019-561994.
Kojien, 5th Edition, Nov. 11, 1998, p. 1796.
Japanese communication, with English translation, dated Dec. 8, 2020 in co-pending Japanese patent application No. 2019-561961.
Canadian communication dated Oct. 22, 2021 in corresponding Canadian patent application No. 3,062,516.
Canadian communication dated Oct. 22, 2021 in co-pending Canadian patent application No. 3,062,519.
Office action dated Jul. 13, 2022 in co-pending U.S. Appl. No. 16/610,595.
Notice of Allowance dated Sep. 12, 2022 in co-pending U.S. Appl. No. 16/610,595.
Notice of Allowance dated Sep. 26, 2022 in co-pending U.S. Appl. No. 16/610,595.

\* cited by examiner

US 11,732,003 B2

MECHANICAL METHOD OF MAINTAINING NARROW RESIDENCE TIME DISTRIBUTIONS IN CONTINUOUS FLOW SYSTEMS

This application claims priority of U.S. Provisional Application Ser. No. 62/504,633 filed May 11, 2017, the disclosure of which is incorporated herein by reference in its entirety.

BACKGROUND

Large-scale production and the economics around purification of therapeutic proteins, especially monoclonal antibodies, is an increasingly important problem for the biopharmaceutical industry. Therapeutic proteins are generally produced in either mammalian cells or bacterial cells which have been engineered to produce the protein of interest. However, once produced, the protein of interest needs to be separated from various impurities such as host cell proteins (HCPs), endotoxins, viruses, DNA etc.

In a typical purification process, the cell culture harvest is subjected to a clarification step for removal of cell debris. The clarified cell culture harvest containing the protein of interest is then subjected to one or more chromatography steps, which may include an affinity chromatography step or a cation exchange chromatography step. In order to ensure viral safety of the therapeutic candidate and to comply with regulatory mandates, viral clearance unit operations are implemented into the purification process. Such steps include Protein A and ion exchange chromatography, filtration and low pH/chemical inactivation. Virus inactivation is typically performed after a chromatography step (e.g. after affinity chromatography or after cation exchange chromatography). In a typical large scale purification process, the chromatographic elution pool containing the protein of interest is collected in a large tank or reservoir and subjected to a virus inactivation step/process for an extended period of time with mixing, which may take several hours to a day or longer, in order to achieve complete inactivation of any viruses that may be present in the elution pool.

In monoclonal antibody (mAb) processing, for example, a sequence of independent unit operations is performed in batch mode, where holding tanks are used to store the material between unit operations and facilitate any necessary solution adjustments between steps. Typically, the material is collected into one tank where the material is adjusted to achieve the target inactivation conditions. This may be through the addition of acid to achieve a low pH target level or it may be through the addition of detergent in a detergent-based inactivation process. Next, the material is transferred to a second tank where it is held at the inactivation conditions for a specified incubation time. The purpose of the transfer is to eliminate risk of droplets on the walls of the first tank which may not have reached the target inactivation conditions and could contain virus particles. By transferring the material to a different tank, this risk is reduced.

Several virus inactivation techniques are known in the art, including exposing the protein solution to certain temperatures, pH's, or radiation, and exposure to certain chemical agents such as detergents and/or salts. One virus inactivation process involves a large holding tank where material is held at inactivation conditions, such as low pH and/or exposure to detergent, for 60 minutes. This static hold step is a bottleneck in moving towards continuous processing.

Virus kill kinetics indicate, however, that the inactivation time could be significantly shorter than 60 minutes, which suggests that the processing time could be significantly reduced, the static holding tank for virus inactivation could be eliminated, and the method could be more amenable to continuous processing and/or flow inactivation.

Recently, there has been a desire to have a continuous process where the unit operations are linked together and manual solution adjustments are minimized. To facilitate this, efforts are being made to develop in-line processing methods to enable in-line virus inactivation as well as other in-line solution adjustments. A challenge in continuous processing is the efficient movement of fluid from point A to point B. An example would be the plug flow movement of fluid through a length of tubing. The flow involved in mAb processing typically falls into the laminar flow regime (Reynolds number less than 2100). In this regime, molecules disperse due to radial diffusion and as a result, a solute pulse spreads axially along the direction of flow. This is known as Taylor dispersion, and is illustrated schematically in FIG. 1. Poiseuille flow for laminar flow leads to a parabolic velocity profile. The leading and trailing ends of the pulse begin as sharp interfaces but become parabolic in shape due to the laminar flow of the fluid. The axial spreading continues over time, and the molecules become more disperse over the length of the tube. The implication of axial dispersion is observed in the resulting concentration profile obtained for a pulse injection of a marker species at the tube outlet, as seen in FIG. 2. The concentration profile reflects a wide distribution of the marker species' residence time. Such varying residence times may result in uncertainty as to whether all of the fluid has had sufficient residence time in the virus inactivation environment or results in over-sizing the system to secure that no molecules exits sooner than expected. As a consequence of ensuring sufficiently long residence times for virus inactivation, the protein (product) is exposed to the inactivation conditions for excessively long residence times which has undesirable consequences such as potential degradation and aggregation.

In continuous or semi-continuous flow systems, it would be desirable to provide a method of maintaining narrow residence time distributions.

Provision of a continuous or semi-continuous flow system for biomolecule purification would be desirable, particularly for protein purification.

SUMMARY

Embodiments disclosed herein provide methods of maintaining narrow residence time distributions in continuous flow systems, particularly applicable to virus inactivation such as during a protein purification process.

Embodiments described herein obviate or minimize the need for using large tanks or reservoirs for performing virus inactivation during a protein purification process, reduce the overall time required for virus inactivation, and/or reduce the overall physical space required to run the virus inactivation operation during a protein purification process, which in turn reduces the overall footprint for the purification process. Further, this increases the certainty that all molecules have been subjected to a minimum residence time providing some safety factor for inactivation assurance while minimizing extended holds.

In some embodiments, a method for inactivating one or more viruses that may be present in a sample in a purification process is provided, where the method comprises maintaining narrow residence distributions in continuous flow systems by separating the fluid into discrete zones or packets as it flows in the axial direction of a flow channel, such as a tube. The flow channel may function as an incubation chamber. This allows for sufficient residence times in the flow channel for all species of the fluid, which in turn allows for virus inactivation as the fluid flows in the flow channel and mixes with one or more virus inactivation agents. The flow channel can be made of a variety of materials and shapes, including circular plastic tubing and "Smart FLEXWARE®" macro fluidic flow path assemblies formed by welding two sheets of plastic together in a pattern to create channels, commercially available from MilliporeSigma (U.S. Pat. Nos. 9,181,941 B2, 9,051,929 B2).

In certain embodiments, the incubation chamber, flow channel or tube is configured to provide efficient radial mixing and minimal axial mixing that results in a narrow or reduced residence time distribution, and wherein the volume of the chamber or tube is not subject to variations due to pressure and temperature. In some embodiments, the incubation chamber, flow channel or tube is a single use chamber or tube and is sterilizable.

In certain embodiments, a method for inactivating one or more viruses that may be present in a fluid sample containing a target molecule (e.g., an antibody or an Fc region containing protein) is provided, comprising subjecting the fluid sample to a Protein A affinity chromatography process or an ion exchange chromatography process to obtain an eluate; continuously introducing the eluate into an axial flow channel to mix one or more virus inactivating agents with said eluate in the flow channel; and causing the eluate to flow in the axial flow channel in discrete packets for a time sufficient to inactive virus. In certain embodiments, the chromatography process is carried out in a continuous mode. The eluate from the affinity chromatography process can be a real time elution from a column entering the system with all of its gradients of pH, conductivity, concentration, etc., or can be a pool of elution then subjected to inactivation after homogenization.

In some embodiments, the in-line incubation chamber, flow channel or tube may be implemented in a process where holding pools or tanks are located immediately upstream, downstream, or both, of the chamber, channel or tube. In some embodiments the in-line incubation chamber, flow channel or tube may be implemented in a process wherein the chamber, channel or tube directly connects two unit operations, such as an upstream Protein A chromatography operation and a downstream cation exchange operation.

DETAILED DESCRIPTION

Figure 1:
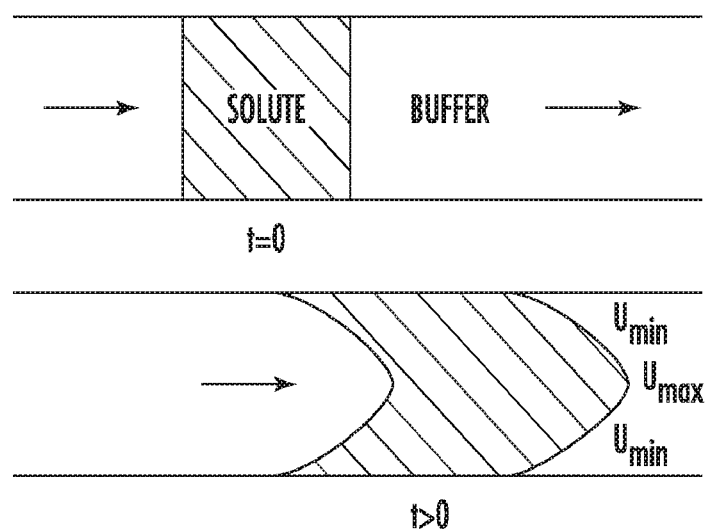
FIG. 1 is a schematic view of the flow of a fluid in a channel.
Figure 2:
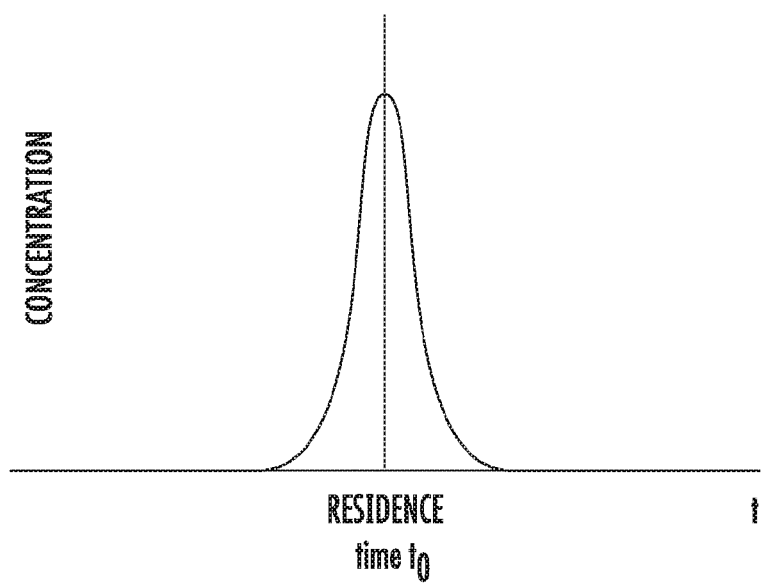
FIG. 2 is a plot of the concentration profile resulting from a pulse input (a finite volume of a marker species injected into the main stream at a rapid rate so as to create a homogeneous plug of the marker species with a concentration profile at each end of the plug approaching a step change) of a marker species in a channel in accordance with the prior art.

The term "in-line" or "in-line operation" refers to a process of moving a liquid sample through a tube or some other conduit or flow channel without storage in a vessel. The term "virus inactivation" or "viral inactivation" refers to the treatment of a sample containing one or more viruses in a manner such that the one or more viruses are no longer able to replicate or are rendered inactive. In methods described herein, the terms "virus" and "viral" may be used interchangeably. Virus inactivation may be achieved by physical means, e.g., heat, ultraviolet light, ultrasonic vibration, or using chemical means, e.g. pH change or addition of a chemical (e.g., detergent). Virus inactivation is typically a process step which is used during most mammalian protein purification processes, especially in case of purification of therapeutic proteins from mammalian derived expression systems. In methods described herein, virus inactivation is performed in a fluid flow channel where the sample is caused to travel in discrete zones or packets. It is understood that failure to detect one or more viruses in a sample using standard assays known in the art and those described herein, is indicative of complete inactivation of the one or more viruses following treatment of the sample with one or more virus inactivating agents.

The term "discrete zone" or "packet" refers to an individually defined volume separated from adjoining volumes by an intervening barrier.

The term "virus inactivating agent" or "virus inactivation agent" or "virus clearance agent" refers to any physical or chemical means capable of rendering one or more viruses inactive or unable to replicate. A virus inactivating agent, as used in the methods described herein, may include a solution condition change (e.g. pH, conductivity, temperature, etc.) or the addition of a detergent, a salt, an acid (e.g., acetic acid, with a molarity to achieve a pH of 3.6 or 3.7), a polymer, a solvent, a small molecule, a drug molecule or any other suitable entity, etc., or any combination thereof, which interacts with one or more viruses in a sample, or a physical means (e.g., exposure to UV light, vibration etc.), such that exposure to the virus inactivating agent renders one or more viruses inactive or incapable of replicating. In a particular embodiment, a virus inactivation agent is a pH change, where the virus inactivating agent is mixed with a sample containing a target molecule (e.g., an eluate from a Protein A bind and elute chromatography step) in a flow channel where the sample is caused to flow in discrete zones or packets.

The term "continuous process" as used herein, includes a process for purifying a target molecule, which includes two or more process steps (or unit operations), such that the output from one process step flows directly into the next process step in the process, without interruption, and where two or more process steps can be performed concurrently for at least a portion of their duration. In other words, in the case of a continuous process, it is not necessary to complete a process step before the next process step is started, as long as a portion of the sample is always moving through the process steps.

Similarly, a "semi-continuous process" may encompass an operation performed in a continuous mode for a set period of time with periodic interruption of one or more unit operations. For example, stopping the loading of feed to allow for the completion of other rate-limiting steps during a continuous capture operation.

Conventional processes for protein purification typically involve cell culture methods, e.g., using either mammalian or bacterial cell lines recombinantly engineered to produce the protein of interest (e.g., a monoclonal antibody) followed by a cell harvest step to remove cell and cell debris from a cell culture broth. The cell harvest step is usually followed by a capture step, which is typically followed by one or more chromatographic steps, also referred to as polishing steps, which usually include one or more of cation exchange chromatography and/or anion exchange chromatography and/or hydrophobic interaction chromatography and/or mixed mode chromatography and/or hydroxyapatite chromatography, size exclusion chromatography, depth filtration or use of activated carbon. A virus inactivation step may also be included after the capture step. The polishing steps are usually followed by virus filtration and ultrafiltration/diafiltration, which completes the purification process.

Biopharmaceutical manufacturing requires the inactivation or removal of viruses (coming from animal derived components, including mammalian cells) for drug safety and to meet the standards set forth by regulatory agencies such as the Food and Drug Administration (FDA). Typical processes involve a number of viral clearance steps that cumulatively provide the necessary protection.

Some processes involve titration of the solution containing the target protein to a low pH in order to cause destruction of any enveloped viruses and viral components. Conventionally, the sample containing the target protein is retained at these conditions for an extended period of time, both because time is needed for virus inactivation but also, and more importantly, to ensure homogeneous mixing for effective virus inactivation. Therefore, in case of large scale processes, the sample containing the target protein is incubated for an extended period of time at a low pH in order to promote efficient virus inactivation, often with mixing. Two separate tanks are often used, where the first tank is used to adjust the pH and the second tank is used for the actual incubation hold.

The pH conditions are established as a balance between a low pH value that is sufficient to cause inactivation and a high enough value to avoid denaturation of the target protein or limit the extent of product degradation. Additionally, the sample must be exposed for a certain amount of time to cause a significant reduction, usually 2 to 6 LRV (log reduction value) in virus activity values.

Parameters that are considered important for a virus inactivation process are pH value, exposure time, the identity of the background solution conditions (e.g., buffer type, buffer concentration), the mAb concentration, and temperature, assuming homogeneous mixing is present. In the case of large-scale processes, mixing poses a challenge due to large volumes and additional parameters, such as mix rate and mass transfer.

In the case of Fc region containing proteins (e.g. monoclonal antibodies), virus inactivation is usually performed following elution from a bind and elute chromatography process step (e.g., Protein A affinity chromatography or cation exchange chromatography) because the pH of the elution pool is closer to the desirable pH for virus inactivation. For example, in processes used in the industry today, the Protein A chromatography elution pool typically has a pH in the 3.5 to 4.0 range and the cation exchange bind and elute chromatography elution pool typically has a pH of about 5.0.

In most processes used in the industry today, the elution pool containing the target protein is adjusted to the pH desired for virus inactivation and held there for a certain length of time, the combination of pH and time having been shown to result in virus inactivation. Longer times are more effective for virus inactivation, especially in case of a large-scale process, however, longer times are also known to cause protein damage and protein denaturation that can lead to the formation of protein aggregates (immunogenic). Extended exposure to low pH may result in precipitation and formation of aggregates, which is undesirable and often requires the use of a depth filter and/or a sterile filter to remove such precipitates and aggregates.

Methods described herein are able to achieve virus inactivation in a continuous or semi-continuous manner, which can significantly reduce the time associated with virus inactivation relative to most conventional processes, and in turn, may reduce the time for the overall purification process.

In some embodiments, the different process steps are connected to be operated in a continuous or semi-continuous manner. In some embodiments, a virus inactivation method, as described herein, constitutes a process step in a continuous or semi-continuous purification process, where a sample flows continuously from, for example, a Protein A affinity chromatography step or an ion-exchange chromatography step to the virus inactivation step to the next step in the process, which is typically a flow-through purification process step. In-line pH inactivation has been proposed in prior art (e.g., Klutz S. et al., Continuous viral inactivation at low pH value in antibody manufacturing, Chemical Engineering and Processing 102(2016) 88-101) but the development of a suitable incubation chamber with a narrow residence time distribution has meant that these chambers are over-sized and may be more difficult to validate.

Figure 12:
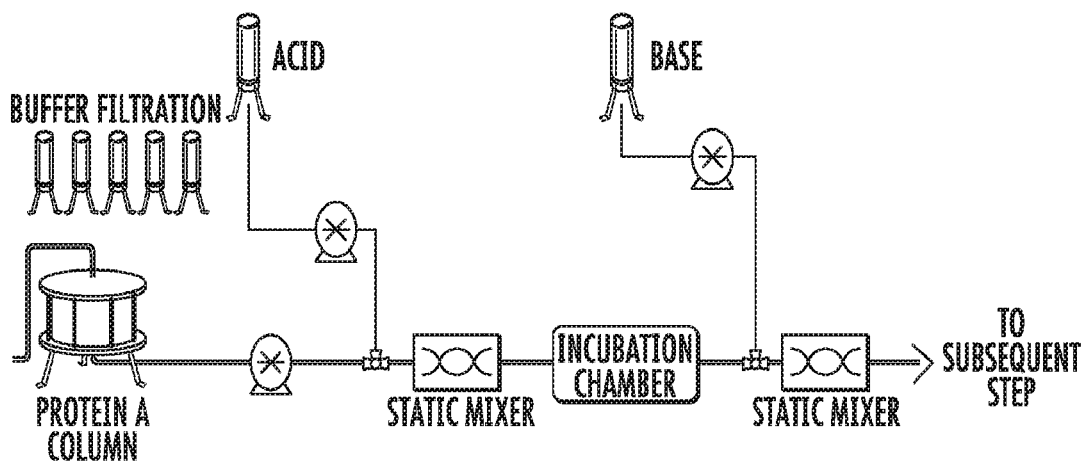
FIG. 12 is a schematic diagram of an in-line continuous inactivation process in accordance with certain embodiments.

In some embodiments, the virus inactivation process step is performed continuously or semi-continuously, i.e., the eluate from the previous process step, such as the previous bind and elute chromatography step (e.g., Protein A affinity chromatography, FIG. 12) flows continuously into the virus inactivation step, which employs one or more fluid channels where the eluate is caused to flow in discrete zones or packets, after which in some embodiments the virus inactivated eluate may be collected in a storage vessel until the next process step is performed, or in some embodiments may be fed directly and continuously to the next downstream process step. For example, with reference to FIG. 12, in certain embodiments Protein A mAb eluate is rapidly brought to a uniform low pH using in-line acid addition with precise syringe pumps & static mixers. Robust low pH is maintained over variable protein feed concentration using 1M acetic acid concentrate. The pH may be verified using sampling and offline sensors. Robust pH control over extended multiday operation may be achieved without a complex continuous feedback control loop and unreliable pH sensors. The inactivation or incubation chamber provides reliable hold time for robust LRV, and a rapid consistent quench to a pH (e.g., 5-7.5) required for a subsequent step.

Figure 3:
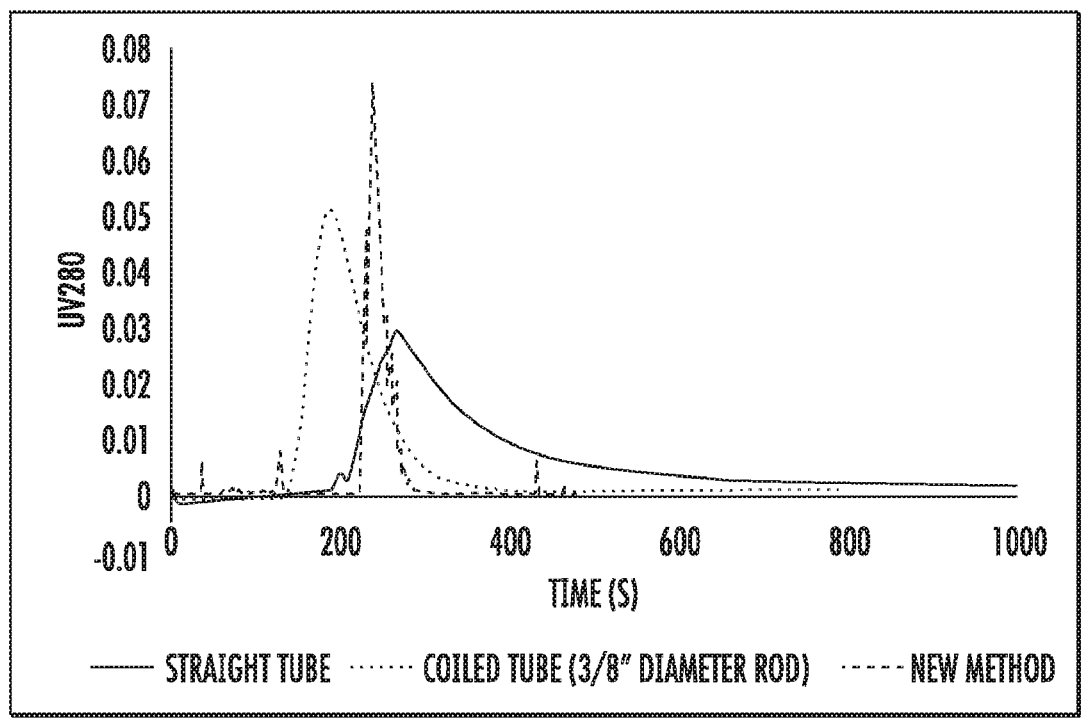
FIG. 3 is a graph of UV exposure vs. time for various flow channels.

In accordance with certain embodiments, narrow residence time distributions are maintained in continuous or semi-continuous flow systems. The residence time distributions are sufficiently narrow (and reduced compared to conventional designs) to achieve effective virus inactivation of fluid sample traveling in the system. Suitable narrow residence time distributions can be quantified based on comparisons to results obtained from conventional designs. Pulse data (e.g., UV absorbance peaks) from different designs can be compared using statistical quantification metrics. For example, a comparison of the amount of time required for the middle 80% of the fluid to exit a flow channel can be made. That is, the spread between the 10% and 90% area values can be made (where $t_{10\%}$ represents the time at which 10% of the fluid has exited the channel, and $t_{90\%}$ represents the time at which 90% of the fluid has exited the channel). This comparison was carried out for the peaks shown in FIG. 3 and is set forth in Table 1 below, using tubing having an ID of ⅛" and a length of 250 inches to equate to a system volume (hold-up volume) of 50 mL. Other methods of analyzing peak characteristics such as those applied by those knowledgeable in the art, for example, moment analysis, could also be leveraged.

TABLE 1

| Method | $t_{10\%}$ (s) | $t_{90\%}$ (s) | Difference between $t_{10\%}$ and $t_{90\%}$ (s) |
|---|---|---|---|
| Straight tube | 251 | 1416 | 1165 |
| Coiled tube (3/8" rod) | 166 | 403 | 237 |
| The present flow channel | 231 | 260 | 29 |

Figure 4:
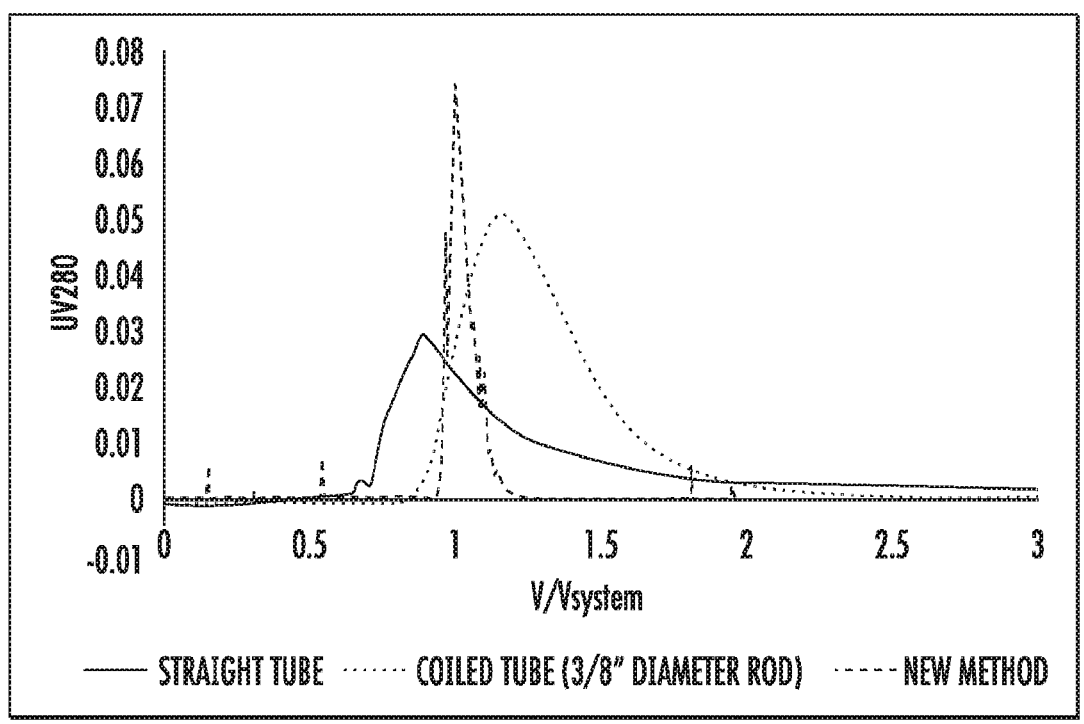
FIG. 4 is a graph of UV exposure vs. volume for various flow channels.

To compare various designs with different system volumes, these data can also be presented as a normalized volume (normalized to the system volume). This is shown in FIG. 4 and set forth in Table 2 below:

TABLE 2

| Method | $(V/V_{system})_{10\%}$ | $(V/V_{system})_{90\%}$ | Difference between $(V/V_{system})_{10\%}$ and $(V/V_{system})_{90\%}$ |
|---|---|---|---|
| Straight tube | 0.84 | 4.72 | 3.88 |
| Coiled tube (3/8" rod) | 1.02 | 2.49 | 1.47 |
| The present flow channel | 0.96 | 1.08 | 0.12 |

In these analyses examples, the 10-90% spread for embodiments disclosed herein is significantly smaller than the values for the conventional designs, and constitute narrow residence time distributions in accordance with the embodiments disclosed herein, which are reduced from the distributions of conventional designs. In the ideal case for plug flow, this 10-90% spread would go to zero.

In some embodiments, narrow residence time distributions are created and maintained by using mechanical methods to separate the fluid into different or discrete zones or packets along the axial direction of a fluid flow channel in which the sample is traveling. A discrete packet is a packet or zone that is separated from another packet or zone by an intervening barrier; any degree of separation which forms a boundary between one volume of the process fluid and an adjacent volume or volumes of the process fluid is a discrete zone or packet. The barrier can be created by mechanically pinching the walls of the fluid channel together (as discussed in greater detail below). The length of the packet separation (i.e., the compressed region length) is not critical; the packets can be separated by a very small length or a much longer length, as long as the size is sufficient to maintain the separation between packets.

In some embodiments, the different or discrete zones or packets of fluid are achieved by applying compressive forces to the exterior of the fluid flow channel, spaced along the axial length of the channel, while the fluid is flowing in the channel, essentially mimicking a peristaltic pump. Separating the fluid into zones or packets minimizes the axial dispersion and mixing of the fluid in the channel. The axial dispersion of residence time will impact the range of residence times a particle may experience. Longer residence time may be more desirable for inactivating virus particles while at low pH. However, a protein particle in the same solution subjected to excessively long residence time at low pH may degrade, which is undesirable. The extent of the minimization of residence time will depend on the sensitivity of the product (e.g., protein) being processed but in any case will be beneficial the lower it is. Thus the amount of dispersion that can be tolerated will depend on the particular application. For virus clearance applications, minimizing the axial dispersion will offer significant advantages in terms of reducing processing time because there will be greater confidence in the virus inactivation within a short window of time.

In certain embodiments, the formation of discrete packets or zones of fluid allows fluid species to be translated axially along the length of a flow channel such that the profile at the channel inlet matches or substantially matches the profile at the channel outlet, adding consistency and certainty to the residence time of the fluid species in the channel.

Sample introduced as a pulse at one end of a flow channel will exit the flow channel in a sharp, well-defined peak at a known time. This has advantages for in-line continuous virus inactivation applications where it is necessary to achieve a target minimum residence time for species flowing through a system. It also can be implemented in systems where mobile phase (e.g., buffer) conditions change or where buffer dilutions occur. This could take place at multiple places within a typical mAb purification process. One example is the adjustment that is often required between a bind-and-elute cation exchange step and a flow-through anion exchange step. The elution pool from the cation exchange step is often at a lower pH and a higher conductivity than the target values for the anion exchange step. In order to efficiently adjust the cation exchange elution pool to the appropriate conditions in a continuous flow system, discrete packets could be formed which would allow for an efficient transition to the new conditions. Sharp transitions zones between different buffer types can be provided, thereby minimizing the amount of time and buffer required, and allowing for in-line buffer dilution or in-line conditioning applications.

Figure 5:
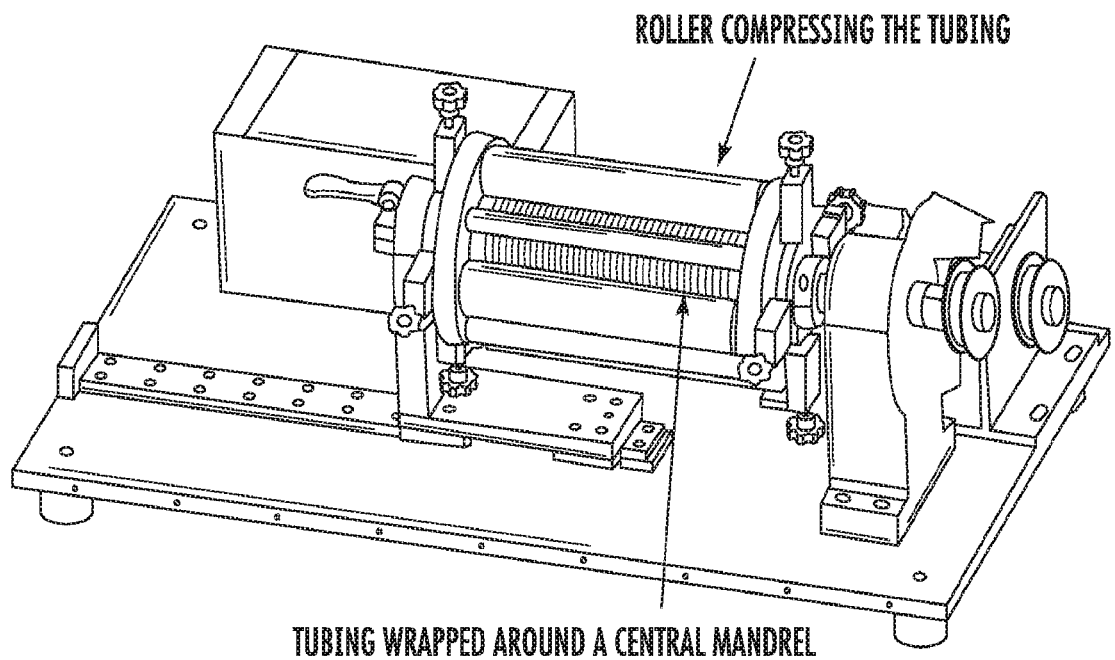
FIG. 5 is a perspective view of apparatus suitable for creating a compressive force on a flow channel to form packets of fluids in accordance with certain embodiments.
Figure 6:
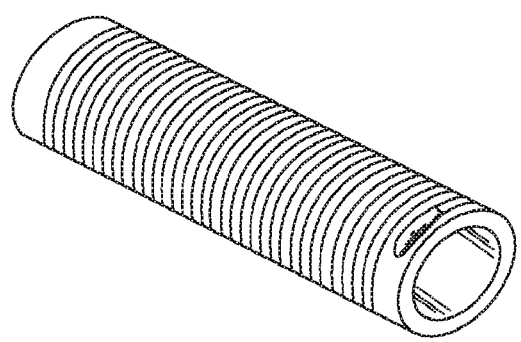
FIG. 6 is a perspective view of a flow channel wound around the mandrel shown in FIG. 5.
Figure 7:
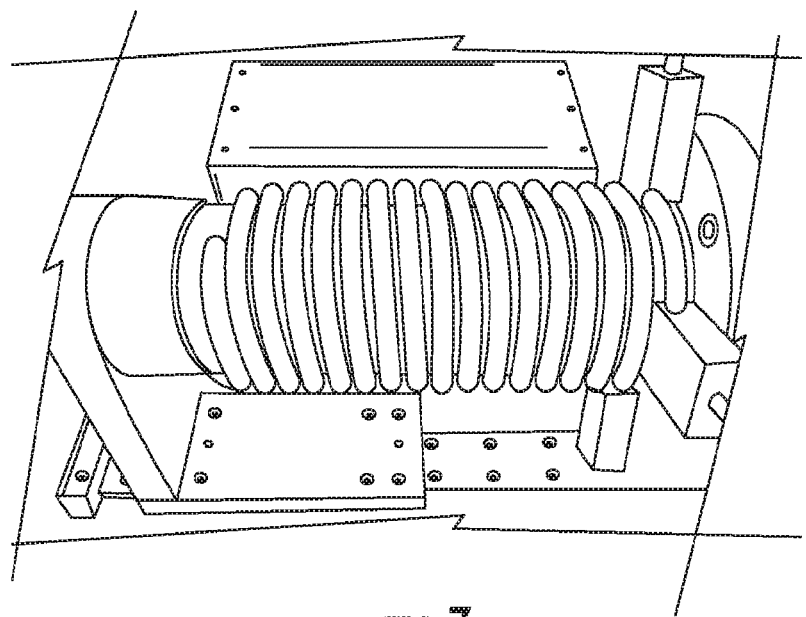
FIG. 7 is a perspective view of a flow channel wound around a mandrel placed in the apparatus of FIG. 5.

Turning now to FIGS. 5-7, there is shown suitable apparatus for applying compressive forces to the fluid channel to create the fluid zones or packets in accordance with embodiments disclosed herein. Many other geometries and configurations could be designed which would produce the same effect, such as those illustrated in FIGS. 13A-13C. FIGS. 6 and 7 illustrate a mandrel 5 around which a fluid channel 10, such as tubing, can be wrapped to fix the fluid channel 10 in place. One or more rollers 15 rotate around the mandrel 5 and apply a constant compressive force to the outside of the fluid channel 10 as they rotate. The fluid inside of the channel 10 is moving axially through the channel as the rollers 15 rotate. The pressure from the rollers 15 keeps the fluid separated into many different zones or packets along the entire length of the fluid channel 10. The separation into zones or packets minimizes axial dispersion of the fluid and therefore provides flow characteristics that are desirable for applications involving the efficient movement of species, such as in-line virus inactivation or transitions from one fluid to another, such as buffer transition, or buffer dilution. The force necessary to completely close off all of the flow channels across one quadrant of the "peristaltic helix" design is a function of the type and size of the tubing used as the flow channel. For example, the force needed to compress 17 revolutions of tubing across one quadrant (each quadrant separated by 2.23" of circumference; that is, the compressive forces are applied every 2.23", the arc length of tubing between rollers) of a helix was 187 lbsf (11 lbsf per revolution of tubing) when using reinforced silicone tubing (⅜" OD, ⅛" ID). The spacing between the rollers dictate the axial length of each packet. Those skilled in the art will appreciate that the foregoing is merely exemplary; other designs could offer other packet sizes.

Figure 13A:
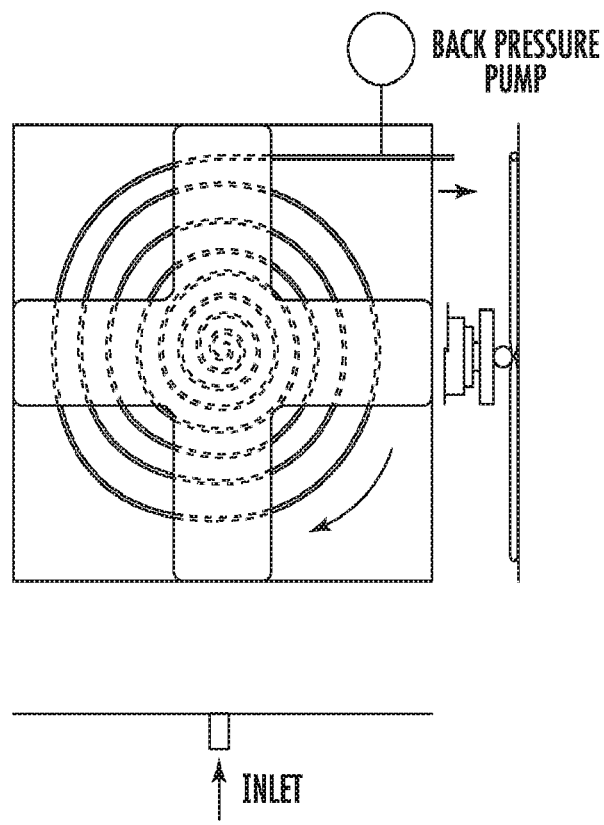
FIG. 13A is a schematic diagram of a windmill design for compressing a flow channel to form packets in accordance with certain embodiments.

In some embodiments, a 'windmill' design could be used which operates on a radial pattern with changing cross-section to maintain constant fluid velocity with a constant angular velocity roller driving. One or more rollers may be attached to a rotating hub. As the hub rotates, the rollers compress the flow channel, forming fluid packets along the flow channel. The flow channel can be made of circular plastic tubing or may be formed from plastic sheets welded together to create channels (e.g., Smart FLEXWARE®). FIG. 13A is an example of a mechanical design in which tubing is arranged in a radial pattern with changing cross-section. One or more rollers are used to compress the tubing as the hub rotates. In the example shown in FIG. 13A, four rollers are shown on the windmill but a different number of rollers could be used depending on the desired fluid packet size.

Figure 13B:
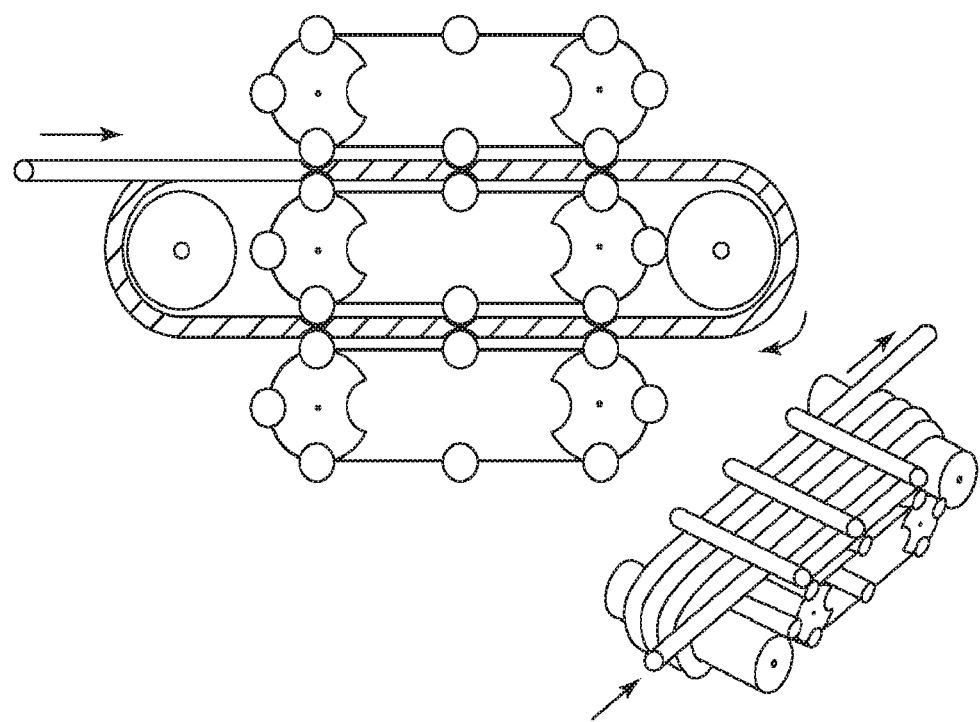
FIG. 13B shows top and perspective views of a conveyor design for compressing a flow channel to form packets in accordance with certain embodiments.

In some embodiments, a 'conveyor' design could be used which involves two rolls with a pair of pinch rollers moving across an array of tubing. The pinch rollers traverse along the gap between the two rolls and then come around again after separating and returning to the other end. The spacing between the pinch rollers is determined based on the desired packet size. FIG. 13B illustrates an example of a mechanical design in which tubing is wrapped around two rolls and is pinched by rollers traversing along the gap between the two rolls.

Figure 13C:
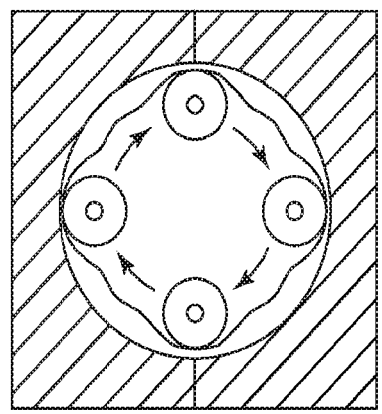
FIG. 13C is a schematic diagram of a roller design for compressing a flow channel to form packets in accordance with certain embodiments.

In some embodiments, rollers could be positioned on the inside of a tubing coil such that they compress the tubing against a fixed outer wall. The spacing between the rollers and the tubing size is determined based on the desired packet size. FIG. 13C illustrates an example of a mechanical compression method in which the rollers are placed on the inside of a tubing coil and the rollers compress the tubing against a fixed outer wall.

The flow rate and tubing length may be selected to target a particular residence time. For virus inactivation applications, the residence time is chosen as the time sufficient to achieve virus inactivation within the flow channel, preferably with some safety factor. For example, where a 30 minute inactivation time is required, a safety factor of 2 can be employed, resulting in a target residence time of 60 minutes in the flow channel. In other embodiments, where virus inactivation takes place in less than 1-2 minutes, a safety factor can be employed and a 4 or 5 minute target residence time in the flow channel is used. The minimum residence time may also depend on regulatory guidance in terms of an acceptable safety factor for virus inactivation.

Suitable nominal residence times include, but are not limited to, 1-2 minutes, 2-4 minutes, 4-6 minutes, 6-8 minutes 8-10 minutes, 10-15 minutes and 15-30 minutes.

The ability to maintain narrow residence time distributions has advantages for virus inactivation processes such as mAb processing where it is imperative for viruses to spend a minimum amount of time at specified inactivation conditions such as low pH, exposure to detergents, etc. By maintaining narrow residence time distributions, it is possible to meet the minimum time requirement for virus inactivation while also minimizing the exposure of the product (e.g., protein/mAb) to the harsh inactivation conditions.

In the case of low pH inactivation, for example, virus inactivating agent such as acid may be added as a side stream into the main feed flow channel. In certain embodiments, a syringe pump may be used that is controlled by a software program to add the desired amount of virus inactivating agent. In some embodiments, a controller for the pump may be provided, the controller having a processing unit and a storage element. The processing unit may be a general purpose computing device such as a microprocessor. Alternatively, it may be a specialized processing device, such as a programmable logic controller (PLC). The storage element may utilize any memory technology, such as RAM, DRAM, ROM, Flash ROM, EEROM, NVRAM, magnetic media, or any other medium suitable to hold computer readable data and instructions. The instructions may be those necessary to operate the pump. The controller may also include an input device, such as a touchscreen, keyboard, or other suitable device that allows the operator to input a set of parameters to be used by the controller. This input device may also be referred to as a human machine interface or HMI. The controller may have outputs adapted to control the pump. These outputs may be analog or digital in nature, and may provide a binary output (i.e. either on or off), or may provide a range of possible outputs, such as an analog signal or a multi-bit digital output. After the agent is added and mixed (e.g., through an in-line static mixer), then it enters the incubation chamber flow channel where it flows through for the target inactivation time. The agent addition amount depends on the acid type, acid strength, and the buffering capacity of the feed solution. The feed solution buffering capacity will depend on many factors including the buffer species, buffer concentration, and mAb concentration. An analogous process could be used for detergent inactivation instead of low pH inactivation.

In accordance with embodiments disclosed herein, fluid sample introduced into a fluid channel will exit the fluid channel with minimal peak broadening. The amount of peak broadening observed when the methods disclosed herein are applied is significantly less than when conventional methods of virus inactivation are employed. FIG. 4 illustrates a comparison of peak broadening resulting from the methods disclosed herein with conventional methods. Peak broadening with a sample injected into a straight tube, a coiled tube (tube wrapped around a rod with a 3 inch diameter) and a tube where discrete fluid packets are induced in accordance with embodiments disclosed herein are shown in FIG. 4. All tubes had the same inner diameter and a length which corresponds to a 50 mL theoretical hold-up volume. A 0.5 mL sample was injected into the tubes initially containing water and after the sample injection, water was passed through each tube at 10 mL/min (corresponding to a nominal residence time of 5 minutes). The resulting UV trace was collected at the tube outlet. The volumes were normalized to the system volume.

In the literature, coiled tubes have been shown to offer advantages over straight tubes due to secondary flow properties (e.g., Dean vortices, U.S. Pat. No. 5,203,002 "Curved channel membrane filtration"). Dean vortices have been implemented specifically for continuous virus inactivation (WO2015/135844 A1 "Device and method for continuous virus inactivation). The peak obtained using the methods disclosed herein is much narrower than that of both the straight tube and the coiled tube, indicating that the fluid species traveling in the flow channel in discrete packets or zones had a narrower residence time distribution in the system.

The methods described herein also result in a smaller physical footprint of the process, e.g., by eliminating the need to use a pool tank for virus inactivation or by minimizing the size of the incubation chamber necessary to inactivate the virus with an appropriate safety factor. In general, there is a growing demand for more flexible manufacturing processes that improve efficiency by reducing the overall physical footprint of the process (i.e., floor space). The methods described herein are able to reduce the overall footprint of a purification process by eliminating large pool tanks that are typically used for virus inactivation.

EXAMPLES

Example 1. Static Low pH Virus Inactivation with Bacteriophage Virus

In this representative experiment, the purpose was to evaluate the inactivation kinetics of an enveloped bacteriophage virus (Phi6) at low pH conditions. The objective was to determine the exposure time required for complete inactivation.

A monoclonal antibody (mAb) was purified by standard Protein A chromatography and prepared at a concentration of 5 mg/mL. The pH was adjusted from pH 6.3 to pH 3.6 using 8.7 M acetic acid. Human serum albumin (HSA) (0.25% v/v) was added for Phi6 stability. Following confirmation of pH, the virus spike was added to the sample reservoir containing the mAb and vortexed to ensure a well-mixed system. The Phi6 target spike level was $1\times10^7$ pfu (plaque forming units)/mL. Within 0.3 minutes of the virus addition, a 1 mL sample was removed and transferred to a tube containing a previously determined volume of 2 M Tris Base, pH 10 to neutralize (pH 6-8) the sample and quench the inactivation step. The tube was vortexed after the base addition. This process of removing and neutralizing a sample was repeated for each time point. These experiments were carried out at room temperature, 22-25° C. Control samples at the initial and final time points were also analyzed. For the control samples, the pH was maintained at the feed pH level (pH 6.3) but the samples were diluted similarly to the actual samples using the background buffer at pH 6.3.

Figure 8:
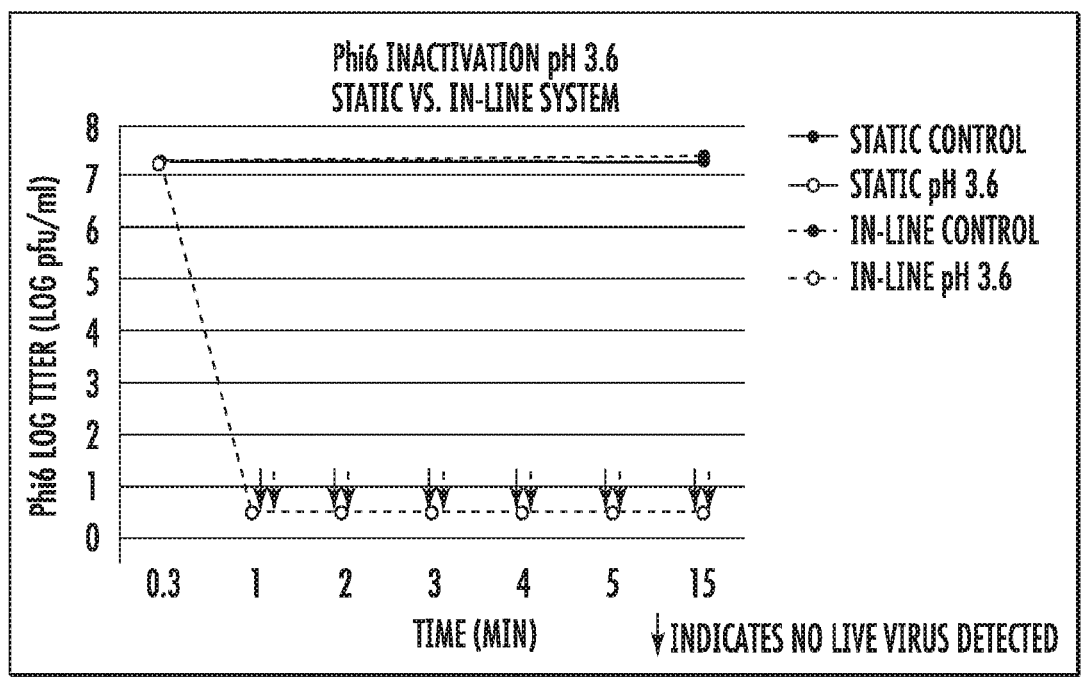
FIG. 8 is a graph showing virus inactivation time for various Phi6 titers.

The neutralized samples were assayed for infectivity using the plaque assay and the results are shown in Table 3. The corresponding Phi6 titers are shown in FIG. 8 as the "static" values.

TABLE 3

| | Inactivation Time (min) | | | | | | Time to Complete Inactivation (min) |
|---|---|---|---|---|---|---|---|
| | 1 | 2 | 3 | 4 | 5 | 15 | |
| Phi6 Log Reduction Values (LRV) | ≥6.8 | ≥6.8 | ≥6.8 | ≥6.8 | ≥6.8 | ≥6.8 | ≤1 |

These results indicate that the pH 3.6 conditions rapidly inactivate Phi6, with complete inactivation occurring within 1 minute. Control samples at 0 and 15 minutes maintained the original titer level.

Example 2. Static Low pH Virus Inactivation with XMuLV Retrovirus

The purpose of this study was to evaluate the virus inactivation kinetics of xenotropic murine leukemia virus (XMuLV, an enveloped virus commonly used for clearance studies of monoclonal antibody products, under low pH conditions. The objective was to determine the exposure time required for complete inactivation.

A monoclonal antibody was purified by standard Protein A chromatography and prepared at a concentration of 18 g/L. The pH was adjusted to a target level of either pH 3.5, pH 3.7, pH 4.0, or pH 4.2 using 8.7 M acetic acid. Following confirmation of pH, the virus spike was added to the sample reservoir containing the mAb and vortexed to ensure a well-mixed system. The XMuLV target spike level was $1\times10^7$ TCID$_{50}$/mL (TCID$_{50}$=Tissue Culture Infection Dose) (4% spike v/v). Within 0.3 minutes of the virus addition, a 1 mL sample was removed and transferred to a tube containing a previously determined volume of 2 M Tris Base to neutralize (pH 6-8) the sample and quench the inactivation step. The tube was vortexed after the base addition. This process of removing and neutralizing a sample was repeated for each time point. These experiments were carried out at room temperature, 22-25° C. Control samples at the initial and final time points were also analyzed. For the control samples, the pH was maintained at the feed pH level but the samples were diluted similarly to the actual samples using the background buffer.

Figure 9:
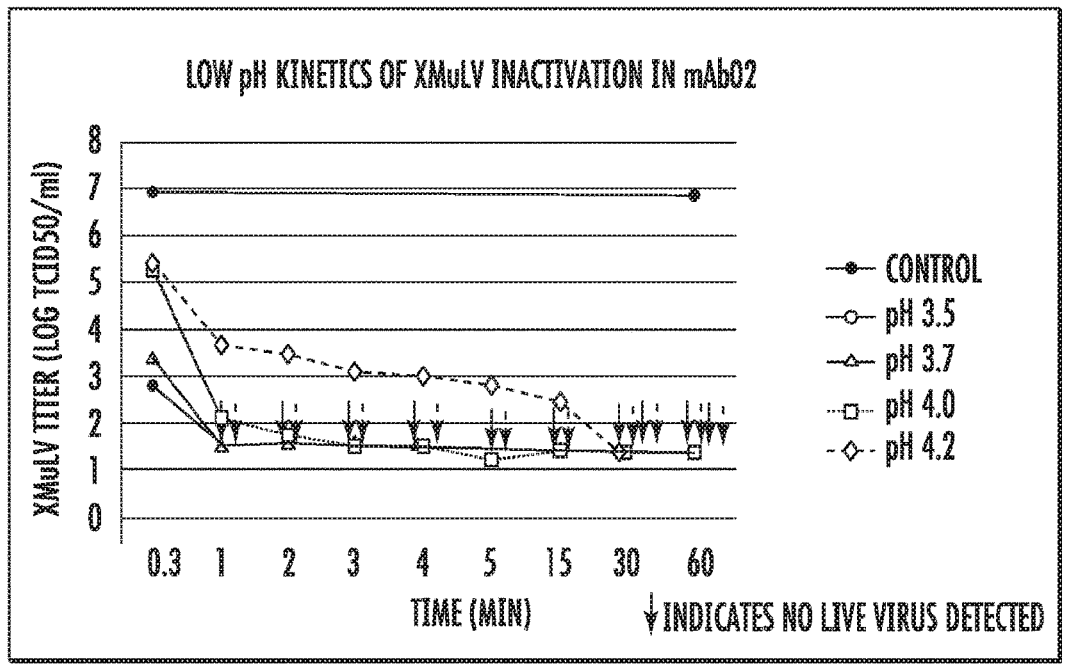
FIG. 9 is a graph showing virus inactivation time for various XMuLV retrovirus titers.

The neutralized samples were assayed for infectivity using the cell-based TCID$_{50}$ infectivity assay using PG4 indicator cells (Bolton G, Cabatingan M, Rubino M, et al. Normal-flow virus filtration:detection and assessment of the endpoint in bio-processing. Biotechnol Appl Biochem 2005; 42: 133-42). To mitigate cytotoxicity and quench the virus inactivation, samples were diluted 1:50 with ten-fold serial dilutions in cell culture media and then 100 μl aliquots of each dilution were added to a 96-well plate. Following incubation at 37° C. in 5% CO$_2$ for 7 days, infected wells were visually assessed for cytopathic effect (CPE). Titers and LRVs were calculated using standard methods (ICH. Guidance on Viral Safety Evaluation of Biotechnology Products Derived From Cell Lines of Human or Animal Origin. In: Use ICoHoTRfRoPfH, ed. Geneva, Switzerland: ICH, 1998). To determine the LRV at each time point, the titer of the time point was subtracted from the titer of the closest control time point. The log reduction values are shown in Table 4. The corresponding titers are shown in FIG. 9.

TABLE 4

| | Inactivation Time (min) | | | | | | | | Time to Complete Inactivation |
|---|---|---|---|---|---|---|---|---|---|
| pH | 0.3 | 1 | 2 | 3 | 4 | 5 | 15 | 30 | 60 | (min) |
| XMuLV LRV at pH 3.5 | 4.0 | ≥5.4 | ≥5.4 | ≥5.4 | ≥5.4 | ≥5.5 | ≥5.5 | ≥5.5 | ≥5.5 | ≤1 |
| XMuLV LRV at pH 3.7 | 3.6 | ≥5.5 | ≥5.5 | ≥5.5 | ≥5.5 | ≥5.7 | ≥5.7 | ≥5.7 | ≥5.7 | ≤1 |
| XMuLV LRV at pH 4.0 | 1.6 | 4.7 | 5.2 | 5.3 | 5.2 | 5.6 | ≥5.4 | ≥5.4 | ≥5.4 | ≤15 |
| XMuLV LRV at pH 4.2 | 1.5 | 3.3 | 3.5 | 3.9 | 4.0 | 4.2 | 4.6 | ≥5.7 | ≥5.7 | ≤30 |

These results indicate that the pH 3.5 and pH 3.7 conditions rapidly inactivate XMuLV, with complete inactivation occurring within 1 minute. Control samples at 0 and 60 minutes maintained the original titer level.

Example 3. Static Detergent-Based Virus Inactivation with Phi6 Bacteriophage Virus The purpose of this study was to examine detergent-based virus inactivation kinetics. In this representative experiment, two different concentrations (0.1% and 1.0% v/v) of a detergent, Triton X-100, were used to inactivate a bacteriophage virus, Phi6. The objective was to determine the exposure time required for complete inactivation.

A monoclonal antibody was purified by standard Protein A chromatography and prepared at a concentration of 15 mg/mL. The virus spike was added and vortexed to ensure a well-mixed system. The Phi6 target spike level was $1 \times 10^8$ pfu/mL. Detergent was added to reach the desired concentrations of 0.1% and 1.0% v/v. At various time points, a sample was removed and quenched by adding it to buffer at a 1:1000 dilution ratio. The tubes were vortexed after the detergent addition. These experiments were carried out at room temperature, 22-25° C. Control samples at the initial and final time points were also analyzed. The control samples were diluted similarly to the actual samples using the background buffer.

Figure 10:
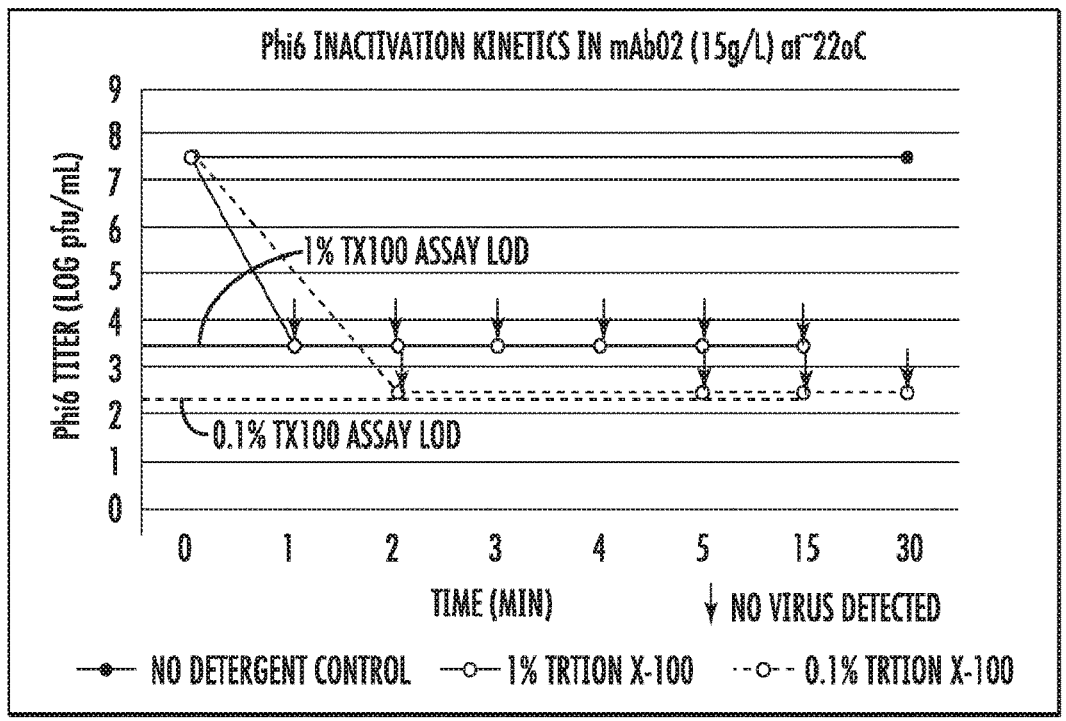
FIG. 10 is a graph showing detergent-based virus inactivation kinetics for Phi 6 titers.

The neutralized samples were assayed for infectivity using the plaque assay and the log reduction values are shown in Table 5. The corresponding Phi6 titers are shown in FIG. 10.

TABLE 5

| | Inactivation Time (min) | | | | | | | Time to Complete Inactivation |
|---|---|---|---|---|---|---|---|---|
| | 1 | 2 | 3 | 4 | 5 | 15 | 30 | (min) |
| Phi6 LRV at 0.1% Triton X-100 | ≥5.2 | ≥5.2 | ≥5.2 | ≥5.2 | ≥5.2 | ≥5.2 | ≥5.2 | ≤1 |
| Phi6 LRV at 1.0% Triton X-100 | ≥6.2 | ≥6.2 | ≥6.2 | ≥6.2 | ≥6.2 | ≥6.2 | ≥6.2 | ≤1 |

These results indicate that the 0.1% and 1.0% Triton X-100 conditions rapidly inactivate Phi6, with complete inactivation occurring within 1 minute. Control samples at 0 and 30 minutes maintained the original titer level.

Example 4. Implementation of Mechanical Method to Create Packets

This representative experiment demonstrates the use of a mechanical method to create packets along a fluid channel.

An apparatus (shown in FIGS. 5-7) was designed to provide compressive forces at defined intervals along a length of tubing. The tubing dimensions were selected based on the volume required to achieve a particular residence time at a specified flow rate (i.e., 10 mL/min). A silicone reinforced tubing with a ⅛" ID and a ⅜" OD was used. This tubing was coiled around a mandrel with a 3" OD. The mandrel had a helix path length of 147". An additional length of tubing connected this apparatus to a main feed pump and another length of tubing was used on the outlet side of the incubation chamber.

The tubing coiled around the mandrel was compressed using a set of 4 rollers simultaneously. These rollers were supported by an apparatus that allowed them to be tightened against the tubing, which forced the tubing to be compressed between the mandrel and the rollers. This mechanically separated the fluid path into packets. The rollers rotated around the mandrel at a rotational speed such that the fluid achieved the target flow rate set by the main feed pump.

Example 5. Residence Time Determination

This representative example provides the method used to determine residence time distribution.

A peristaltic pump was used to pump a feed solution containing a marker species (riboflavin, 0.2 mg/mL) through a tube, an incubation chamber, and into a UV detector. The feed flow rate was 10 mL/min. The incubation chamber utilized the mechanical method described in Example 4 to create packets of fluid within the system. The incubation chamber consisted of 147" of silicone reinforced tubing (⅛" ID) inside of the mechanical apparatus. An additional 30" of tubing was attached to the inlet and outlet incubation chamber tubing. These additional tubes had an internal diameter of ⅛" and were filled with helical static mixers in order to minimize dispersion. The tubing on the outlet of the incubation chamber connected the chamber to the UV detector.

The inlet tube was connected to a buffer reservoir. Initially, the entire system was filled with water. With the flow stopped, a fixed volume (0.5 mL) of marker species (riboflavin) was added into the tube upstream of the incubation chamber. The flow was set to 10 mL/min and water was used to push the marker species through the system. The signal from the UV detector as a function of time was used to determine the marker species' residence time in the system.

Example 6. Virus Residence Time Distribution

This representative example demonstrates residence time distribution of a virus through an incubation chamber. The system was set up as described in Example 5 where a mechanical method was implemented to create fluid packets within the incubation chamber.

Figure 11:
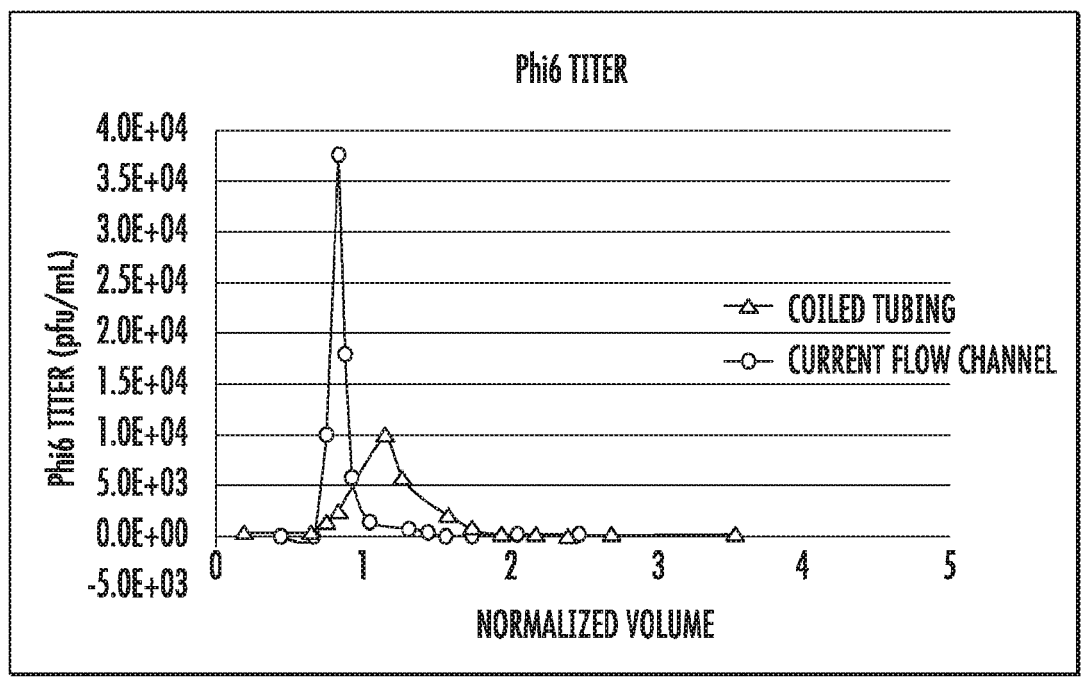
FIG. 11 is a graph of residence time distributions of Phi6 virus in coiled tubing and a conventional flow channel.

Phi6 virus was used as the marker species. The Phi6 target spike level was $1 \times 10^7$ pfu/mL in buffer. The system consisted of a buffer reservoir at the tubing inlet, a length of tubing inside of the incubation chamber which was under mechanical compression, and an outlet tube connecting the incubation chamber to a UV detector. Initially, the system was filled with buffer. Then, a 5 mL sample of Phi6 virus was injected into the system. The flow rate was set to 10 mL/min and buffer was used to push the marker species through the system. Samples were collected at the tubing outlet and assayed for infectivity using the plaque assay. The results are shown in FIG. 11, where the Phi6 titer is plotted as a function of normalized volume. The volume was normalized to the system volume. These experiments were carried out at room temperature, 22-25° C.

A narrower peak was observed for the current flow channel which implemented the mechanical compression method. These results indicate that the mechanical compression method provided a narrower virus residence time distribution than the coiled tubing.

Example 7. Virus Inactivation Using a Continuous Flow System

This representative example describes the use of a continuous flow system to carry out low pH virus inactivation.

A system consisting of a main feed pump, an acid addition pump, and a base addition pump was used to inactivate virus under continuous flow conditions. A mAb solution was spiked with Phi6 and was connected to the main feed pump inlet. The Phi6 target spike level was $1 \times 10^8$ pfu/mL. The acid was 1 M acetic acid and the base was 2 M Tris Base solution. The feed flow rate was set to 1 mL/min. Acid was added into the main stream at a flow rate of 0.75 mL/min. The fluid then passed through a static mixer and a length of tubing designed to contain a particular volume (targeting a desired residence time). Different lengths of tubing were used to contain the required volume for each target average residence time (1, 2, 3, 4, 5, 15 min) after accounting for the dead volume from the valves and pH probe between the acid addition point and the beginning of the incubation chamber. In all cases, the tubing had an inner diameter of ⅛". At the outlet of the incubation chamber, the material was neutralized by the addition of base into the main line at a flow rate of 0.4 mL/min. The fluid passed through another static mixer and then the neutralized samples were collected at the outlet and assayed for infectivity using the plaque assay. The log reduction values are shown in Table 6. These experiments were carried out at room temperature, 22-25° C. Control samples were also assayed. For the control samples, the pH was maintained at the feed pH level but the samples were diluted similarly to the actual samples using the background buffer. The corresponding Phi6 titers are shown in FIG. 8 as the "in-line" values.

TABLE 6

| | Inactivation Time (min) | | | | | | Time to Complete Inactivation |
|---|---|---|---|---|---|---|---|
| | 1 | 2 | 3 | 4 | 5 | 15 | (min) |
| Phi6 LRV | ≥6.8 | ≥6.8 | ≥6.8 | ≥6.8 | ≥6.8 | ≥6.8 | ≤1 |

These results indicate that the virus inactivation occurred within 1 minute using the in-line continuous inactivation system. Control samples at 0 and 15 minutes maintained the original titer level.

These data from the in-line system are identical to the data obtained in Example 1 using static low pH inactivation conditions for Phi6 virus, demonstrating equivalence between the two approaches.

What is claimed is:

1. A method for inactivating one or more viruses in a sample containing a target molecule, wherein the method comprises continuously exposing said sample to virus inactivation conditions, followed by causing the sample to flow in a flow channel in discrete packets by applying compressive force to the flow channel during a process for purifying said target molecule, wherein said compressive force is caused by compressing tubing coiled around a mandrel, said tubing defining said flow channel.

2. The method of claim 1, wherein said flow channel has an outer wall, and wherein said compressive force is created by pinching said outer wall.

3. The method of claim 2, comprising pinching said outer wall with one or more rollers.

* * * * *